United States Patent [19]

Bay

[11] Patent Number: 5,064,652
[45] Date of Patent: Nov. 12, 1991

[54] WOUND DRESSING

[76] Inventor: Michael Bay, 3974 Mollens, Vallais, Switzerland

[21] Appl. No.: 435,420
[22] PCT Filed: Apr. 21, 1988
[86] PCT No.: PCT/EP88/00361
  § 371 Date: Nov. 9, 1989
  § 102(e) Date: Nov. 9, 1989
[87] PCT Pub. No.: WO88/08310
  PCT Pub. Date: Nov. 3, 1988

[30] Foreign Application Priority Data

Apr. 22, 1987 [GB] United Kingdom ............... 8709498

[51] Int. Cl.⁵ ...................... A61L 15/00; A61K 37/36
[52] U.S. Cl. ...................... 424/445; 424/81; 424/487; 514/944
[58] Field of Search ............ 424/445, 81; 514/944

[56] References Cited

U.S. PATENT DOCUMENTS

| | | | |
|---|---|---|---|
| Re. 27,401 | 6/1972 | Wichterle et al. | 524/916 |
| 3,419,006 | 12/1968 | King | 424/445 |
| 3,963,685 | 6/1976 | Abrahams | 526/230 |
| 4,060,678 | 11/1977 | Steckler | 428/81 |
| 4,267,295 | 5/1981 | Gallop et al. | 424/81 |
| 4,857,334 | 8/1989 | Korol et al. | 424/445 |

Primary Examiner—Thurman K. Page
Assistant Examiner—E. J. Webman
Attorney, Agent, or Firm—Ostrolenk, Faber, Gerb & Soffen

[57] ABSTRACT

A sterile sealed flexible package contains a transparent sheet-form wound dressing which comprises a wholly synthetic hydrophilic water-insoluble cross-linked polymer swollen with an aqueous liquid. The package is formed by introducing the sheet-form polymer and aqueous liquid into the flexible package, sealing the package and then sterilizing it in an autoclave in which the temperature and pressure are independently variable. The polymer is usually formed by polymerizing ethylenically unsaturated monomers, usually acrylic monomers, e.g. hydroxy alkyl (meth) acrylates and/or (meth) acrylic acid, with copolymerizable ethylenically unsaturated cross-linking agent, and is capable of absorbing at least its own dry weight of 0.9% by weight saline. The swollen polymer gel is used as a wound dressing.

14 Claims, No Drawings

WOUND DRESSING

The present invention relates to a package comprising a wound dressing packed in a sterile container, and a process for producing sterile packages of this type.

U.S. Pat. No. 3,428,043 describes a bandage of water-swellable hydrophilic polymer with a co-extensive fabric reinforcement, that is supplied dry and contains therapeutically active ingredients. There is no disclosure of any process of sterilisation of the bandage. One problem with the product described is that it is brittle when it is dry so that even with the reinforcement the polymer foil may crack and become discontinous. The reinforcement, necessary because the gel is insufficiently strong when swollen, renders the bandage opaque preventing observation of the underlying wound. Furthermore the most serious problem is that to be used wet the bandage has to be swollen before application to the wound which is inconvenient for the nurse or doctor. The incorporation of fabric reinforcement during manufacture is inconvenient.

U.S. Pat. No. 3,520,949 describes a water-free polymerisation to make water-swellable hydrophilic articles for various uses. It is stated that the articles themselves can be sterilised by boiling. One of the uses is as a bandage reinforced with Dacron fabric and containing medication for slow release to a wound. The bandage is presented in its dry form and must be pre-swollen before use. This bandage has all the disadvantages of that described in U.S. Pat. No. 3,428,403. Although sterilisation by boiling is possible for small articles which are fairly sturdy, it is liable to cause damage to thin sheet materials. Sheets are particularly difficult to handle when they are large.

In U.S. Pat. No. 3,419,006 cross-linked poly(alkylene glycol) gels are used as wound dressings. The polymer is highly swellable, and a gel swollen with pure water may contain about 1-20% polymer. The gels may be autoclaved in a petri dish apparently containing water, the dish being sealed in a plastic bag. According to the description the gel appears to be chopped in a blender with the water and the dispersion autoclaved after bubbling with nitrogen. The gel sheets are insufficiently strong to be used unsupported and in practice must always be strengthened by embedded mesh or gauze and often also a polymeric sheet backing.

In DE-A-2725261 a transparent sheet of a hydrophilic polymer gel is swollen with water and, usually, therapeutically active substances. All the products exemplified are made by polymerisation of water-soluble ethylenically unsaturated monomer in the presence of a gellable high molecular weight substance, e.g. a carbohydrate or a protein. The swollen dressings can be supplied packed in pouches of, e.g. metal or plastics foil, in its swollen condition. It is stated that the packed bandages should be sterile but there is no disclosure of how this is achieved.

In a patent of addition, DE-A-2849570 and U.S. Pat. No. 4,556,056 the gels are dried before storage. When presented in this form the material has the problems discussed above.

In a further improvement of the product described in DE2849570 the polymer is provided in dry powder form as described in U.S. Pat. No. 4,554,156. The powder may be applied direct to a wound or is applied mixed with a little water to form a paste. It is stated that the paste may be supplied in a sterile syringe but there is no disclosure as to how sterility is achieved. According to the specification, on use the particles join to form a coherent film. One of the reasons that the polymer is provided in particle form is that this makes removal of excess monomer from the polymer product easier. Use of this product is highly inconvenient, application of a powder is inconvenient, premixing of the powder with the water is also an undesirable extra step for a nurse or a doctor and application of a paste from a syringe can be messy. All the methods make it difficult or impossible to provide a smooth film of uniform thickness for optimum healing. Furthermore particulate mixtures may not always form a coherent film and any discontinuities may allow ingression of bacterial, viral or fungal contaminants. Even if the particles do form into a coherent film, this can easily disintegrate on removal so that stripping of the dressing is complicated.

U.S. Pat. No. 3,963,685 also describes wound dressings comprising powdered swellable hydrophilic polymer. The polymer was chopped in a blender, then purified by teaching with several changes of water, then dried and ground. The pressing is applied by depositing polyethylene glycol onto a wound then shaking the powder from a salt shaker. Other powder type bandages are described in U.S. Pat. Nos. 3,577,516 and 4,303,066. In each of these specifications the bandage is applied by the application of at least two separate components, one of which comprises particles of hydrophilic polymer, optionally containing therapeutically active ingredients, and the other of which comprises a liquid plasticiser for the polymer. On contact with the plasticiser the polymer forms a coherent film. It is generally inconvenient to have to apply two separate components and spraying of wounds can be uncomfortable for the patient. Furthermore it is difficult or impossible to achieve an even film of an appropriate thickness for optimal healing.

According to the invention there is provided a sterile sealed flexible package containing a transparant sheet-form wound dressing which comprises a wholly synthetic hydrophilic water-insoluble cross-linked polymer swollen with an aqueous liquid, in which the polymer is capable of absorbing 0.9% by weight saline to form a gel containing at least 50% by weight of saline.

The polymer from which the wound dressing is formed is often such that it will absorb between 1 and 100, or more, times its dry weight of water. Since the aqueous liquid in the wound dressing may contain disolved substances, for example inorganic salts and/or organic compounds discussed below in greater detail) the swellability of the polymer in that liquid is likely to be lower than in pure water. Preferably the polymer is capable of absorbing the aqueous liquid in an amount in the range 0.5 to 50 times of its own dry weight, more preferably above 1 or 1.5, most preferably from 2 or 3 to 20 times its own weight, for example up to about 10 times its weight. The swellability of the polymer is as high as possible in order to improve the oxygen and water-vapour permeability of the wound dressing so that when the dressing is in place on a wound the passage of oxygen to the wound is maximized to aid the healing process. Preferably the DK-value (a standard measure of gas permeability) of the dressing when fully swollen in 0.9% by weight saline is at least 20, preferably in the range 20 to 35.

In the package the wound dressing could be swollen by less than the total amount possible, however, it is preferably fully swollen by the aqueous liquid and so the package may contain excess impregnant liquid.

The polymer is preferably formed from ethylenically unsaturated monomer which preferably includes acrylic monomer. The monomer most preferably comprises hydroxy alkyl (meth) acrylate, for example those in which the alkyl group has 2 to 4 carbon atoms. Examples of such monomers are hydroxyethyl acrylate (HEA), hydroxyethyl methacrylate (HEMA), hydroxypropyl methacrylate, hydroxypropyl acrylate and hydroxytrimethylene acrylate. The monomers preferably comprise HEA and/or HEMA. Such hydroxy alkyl (meth) acrylates are generally co-polymerised with one or more co-monomers which may be hydrophilic or hydrophobic and which are selected to impart specific chemical or physical properties to the resulting copolymer Examples of co-monomers are alkyl (meth) acrylates, alkoxy alkyl (meth) acrylates, polyalkylene glycol (meth) acrylates, (meth) acrylic acid, (meth) acrylamide, styrene, N-vinyl lactam, e.g. N-vinyl pyrrolidone.

The preferred polymers are formed from a major amount, i.e. 50 to 100%, of hydroxy alkyl (meth) acrylate, with a minor amount, i.e. 50 to 0% of a co-monomer. The preferred mixture comprises 50 to 100%, more preferably 75 to 99%, most preferably 90 to 98% HEMA and/or HEA with minor amounts of co-monomer, preferably a hydrophilic co-monomer.

The polymer is preferably cross-linked, cross-linking rendering it insoluble and giving it physical strength. Cross-linking is preferably covalent and is generally achieved by incorporating into the polymerisation mixture a di- or poly-functional ethylenically unsaturated compound in an appropriate amount, generally less than 2% by weight of the monomer mixture for example in an amount in the range 0.001 to 2%, preferably 0.05 to 1.5%, generally in the range 0.05 to 1%. Examples of cross-linking agents of this type are well known in the art and may include di- or tri-esters of (meth) acrylic acid, for example alkylene di- (meth) acrylates, generally in which the alkylene has from 2 to 4 carbon atoms, or di- or poly-alkylene glycol (meth) acrylates, generally in which the alkylene groups have from 2 to 4 carbon atoms, and also alkylene bis (meth) acrylamides, usually methylene bis (meth) acrylamide.

The use of polymers formed from ethylenically unsaturated monomer is greatly preferred to polymers of alkylene glycols since the polymerisation can be conducted in a single step whereas in U.S. Pat. No. 3,419,006 the polymer is formed in one step and then cross-linked in another step. Also the polymerisation process and degree of cross-linking are far easier to control and the starting materials are easier to handle. The resultant gel is also strong and even large sheets of swollen gel can be handled without being damaged or requiring strenthening backing or embedded gauze.

The polymerisation may be carried out without any liquid diluent or may be carried out in the presence of water or other suitable diluent. Polymerisation of aqueous solutions of monomers is described in U.S. Pat. No. 2,976,576. Polymerisation in the substantial absence of liquid diluents is described in U.S. Pat. No. 3,520,949. Polymerisation in the presence of non-aqueous diluents is described in GB-A-2097805 which describes the polymerisation in the presence of an ester of boric acid and a compound containing 3 or more hydroxyl groups. In EP-A-0182659 polymerisation is carried out in the presence of a range of water-displaceable solvents, including ester reaction products of carboxylic acids or anhydrides and polyols, often di-functional carboxylic acids, and polyols themselves and mixtures. All the methods described in those references may be used to form the polymer used in the present invention.

The polymerisation is initiated by any known means, for example by using thermal initiators, and/or redox initiators and/or may be initiated using irradiation, optionally including an irradiation-sensitive catalyst. The irradiation may comprise u-v irradiation, electron beam irradiation or irradiation from a radioactive source. Curing agents suitable for use with these forms of irradiation are well known in the art.

Although the polymer may be formed into the desired shape after polymerisation, it is generally polmerised to the desired shape, i.e. as a sheet. The polymerisation mixture is therefore polymerised within a mould or, usually, the polymerisation mixture is cast onto a flat surface, optionally covered with a protective sheet substance and then polymerised. The layer of polymerisation mixture may be in the range 0.1 to 2 mm, preferably 0.2 to 1 mm, more preferably about 0.5 mm thick.

Following completion of the polymerisation the polymer must be washed to rid it of any low molecular weight contaminants, which may comprise for instance excess unpolymerised monomer. Since the polymer is to be used in direct contact with the body, it is most important for excess monomer to be washed out of the polymer. Washing can be carried out by any of the known techniques which are suitable for this. The washing process may comprise several sequential washes using demineralised water or using water of different conductivities in sequential steps. One suitable process comprises soaking the dressing in successively more conductive water.

The wound dressing may comprise one or more suitable therapeutically active substance. Examples of suitable active substances are antibacterials, antiseptics, antibiotics, nutrients, anaesthetics, analgesics, anti-inflammatories and the like. Such substances can be incorporated into the wound dressing by being dissolved in the aqueous impregnant liquid. The polymer of the wound dressing is permeable to these types of substances so that they can difuse through the wound dressing. The dressing therefore acts as a sustained release preparation for the substance. The impregnant liquid is perferably based on physiological saline, sometimes buffered saline.

One particularly preferred type of active substance for which the wound dressings of the invention are suitable as carriers are hormones which improve the rate of healing of wounds. These hormones are polypeptides and are generally classified as growth factors. Examples of suitable hormones are transforming growth factors (TGF) of which many have been identified, e.g. $\alpha$-TGF, epidermal growth factor EGF and vaccinia growth factor VGF although other growth factors may be usefully incorporated, for example insulin. Another polypeptide which has been found to be useful in increasing the rate of wound repair is fibronectin.

It has been reported that topical application of certain growth factors improves wound healing and particularly when a growth factor is continuously supplied to a wound. In Science, 18th March, 1983, p 1329–1331, salivary gland and kidney TGF, sometimes in the presence of EGF were reported to accelerate the wound healing. In Science, 16th January, 1987 $\alpha$-TGF and VGF, as well as EGF, were all found' to accelerate wound repair. In Proc. Natl Acad. Sci (USA) 1985, 82 p 7340 to 7344 slow release of EGF was found to accelerate the process of wound repair.

The package in which the swollen polymer is contained must be moisture proof. A suitable package is formed from thin foil such as metal or plastics foil, for example formed of alkylene, usually ethylene and/or propylene, vinyl or vinylidene polymers, or polyesters. Suitable the foil is formed of polypropylene. The foil may be formed into a pouch by known methods, e.g. by adhering or heat sealing the edges of a pair of superposed foils or a pouch made by folding a foil. The swollen polymer wound dressing is inserted into the package before all of the edges are sealed. Processes for packaging moist sheet materials into pouches of this type are known. After sealing off the packages they are sterilised and this process forms another aspect of our invention.

Thus in the invention there is further provided a new process for producing a package containing a wound dressing in which a wholly synthetic hydrophilic water-insoluble transparent polymer, that is capable of absorbing 0.9% by weight saline to form a gel comprising at least 50% saline by weight, which is swollen with an aqueous liquid is introduced into a flexible package, the package is sealed and the sealed package is sterilised by heating whilst exerting external pressure on the package. Exerting pressure on the outside of the package prevent it from bursting during heating due to the increased internal pressure created when the package, which contains a liquid, is heated. The sterilisation is generally steam sterilisation although air or a mixture of air or other gas and steam may be used to heat the package. Conventional temperatures and times are used, thus a suitable steam sterilisation process would be carried out at a temperature of about 121° C. for a period of about 15 to 20 minutes. The external pressure may be supplied by retaining the sealed package within a mould, preferably however it is achieved by increasing the gas pressure in the environment of the package during heating. Sterilisation is preferably by heating the package in an autoclave, preferably an autoclave in which the temperature and pressure inside the chamber can be controlled independently. Autoclaves of this type are known, one type being described in EP-A-0067420.

In the process the polymer is made as described above and is washed to remove low molecular weight contaminants before being sealed in the package. In a further aspect of the process, a therapeutically active substance, for example of one of the types described above is introduced into the impregnant solution of a wound dressing. Where the active substance is capable of withstanding the temperatures reached during steam sterilisation, it may be incorporated into the aqueous liquid impregnant before the package is sterilised. In some circumstances, for example, where the active substance is sensitive to high temperatures, then it may be incorporated into the impregnant liquid after sterilisation. In such instances the package may be provided with means allowing injection of active substance following sterilisation so that the active substance can be supplied to the dressing. This avoids the necessity of the user applying a separate compositions to the patient. However, since the polymer is permeable to the active substances, it is possible to apply the active substance to the external surface of a wound dressing which has already been applied to a wound.

In order to use the wound dressing the package merely has to be opened and the swollen polymer gel applied direct to the wound area. The dressing should in general totally cover the wound and so the dressings are usually supplied in various sizes. The sheet is generally 0.1 to 5, preferably 0.5 to 2 mm thick when fully swollen with physiological saline. The gel is strong enough to handle even when it is relatively thin, for example less than 2 or 1 mm thick. The package may be provided with a nick, tear tab or thread or other means to facilitate its opening.

The wound dressing is preferably maintained in a swollen condition, preferably in its completely swollen condition, whilst it is maintained in contact with the wound. It is therefore sometimes necessary to apply a covering over the wound dressing which is kept moist. This serves also to retain the dressing in position. The transparency of the wound dressings allows the progress of healing to be observed without removal of the dressing whilst the dressing acts as a barrier for preventing microbes from coming into contact with the wound and also to prevent the wound from drying up whilst allowing oxygen to defuse through to the wound, and it is thought that under these conditions optimal wound healing is achieved. The gel is found to be non-adherent to wounds and so is easily removed during or after healing without disturbing the underlying tissue.

The wound dressings of the invention are preferred over those provided in the prior art, in particular over those in DE-A-2725261. The use of wholly synthetic monomers allows the product to be more closely defined than polymers containing natural substances. Furthermore it would be impossible to steam sterilise the polymer mixtures provided in DE-A-2725261 since if the natural substance was a protein then this would be denatured at the temperatures attained in steam sterilisation and if the natural substance were a carbohydrate then it would be hydrolised and even solubilised during sterilisation. Furthermore these natural products are not well defined and can vary widely, making the production process more difficult and leading to variations in the properties of the product polymer which is highly undesirable, especially for clinical use. The gels of DE-A-2725261 containing natural substances would furthermore be degraded by enzymes present on a wound, in use, and would act as good support for bacterial growth, which is disadvantageous. The gels of the present invention will not have these problems.

The following is an example of the invention:

EXAMPLE 1

97.5 parts HEMA (containing 200 ppm of the polymerisation inhibitor hydroquinone monomethyl ether HQME), 1 part HEA (containing 200 ppm HQME) and 0.75 part of methacrylic acid (MAA) with 0.5 parts a cross-linking monomer comprising ethylene glycol di-methacrylate (EGDMA), were mixed together 0.25 parts of a curing agent (Darocur 1173) was added to the polymerisation mixture which was then cast onto a flat surface to a thickness of 0.5 mm. The mixture was cured by irradiating with UV at a wavelength of 365 nm using an intensity of 200 mW/cm$^2$ for a period of about 60 minutes.

Following polymerisation the polymer was removed from the surface and was washed by immersion in water having a conductance of 750 microsiemens/cm$^2$ for about 12 hours followed by immersion in water having a conductance of 1550 microsiemens/cm$^2$ for a further period of about 12 hours. The polymer was then immersed in a 0.9% sodium chloride solution made up in redistilled water for several hours. Pieces of the gel sheet were then packed in polypropylene foil containers containing excess inpregnant sodium chloride solution. The pouches were heat sealed and were then sterilised in an autoclave at a temperature of 121° C. for a period of 15 to 20 minutes.

The polymer produced by this process was capable of absorbing saline to form a gel having 70% by weight inpregnant liquid.

The swollen gel could be used by application direct onto a wound.

In order to study whether the gel dressing could be used as a vehicle that could be used to deliver growth hormone to a wound and thereby stimulate wound healing, the proliferation of vessels in contact with epidermal growth factor-containing dressings was investigated.

Ten pieces of 10×10 mm of gel sheet were immersed in a solution containing epidermal growth factor in phosphate-buffered saline pH 7.2 at a concentration of 1 microgram/5 ml buffer. One day later the gel sheet was transplanted to subcutaneous sites of the dorsal back of nude mice. Five days after transplantation the mice were sacrificed, and the degree of vessels proliferating in relationship to the connective tissue under the gel dressing was read in a stereomicroscope. Pieces of the gel dressing immersed in physiological saline served as control.

In all ten cases investigated vessel proliferation was seen in relationship to the gel dressing containing EGF. The proliferation was both seen under the gel dressing which probably indicated the release from the surface of the dressing and from the cut edges. No vessel proliferation and no tissue reaction was seen in relationship to the controls. Histological specimens indicated multiple vessels beneath gel dressing which has been immersed in epidermal growth factor, but no histological reactions, neither vessel proliferation nor inflammation reaction, in the control tissue.

The gel dressing itself therefore appears to have no adverse physiological effects in contact with a wound and acts as a suitable delivery system for therapeutically active substances to a wound, in this case for supply of EGF to increase the rate of wound healing.

EXAMPLE 2

30 parts HEMA containing (200 ppm HQME), 68 parts HFA (containing 200 ppm HQME), 0.5 part EGDMA, 0.5 part MAA and 0.5 part Darocur 1173 were polymerised using the same process used in example 1. The polymer was capable of absorbing saline to form a a gel having 65% by weight impregnant liquid.

I claim:

1. A sterile sealed, moisture-proof flexible package containing a transparent self-supporting sheet-form wound dressing comprising a wholly synthetic hydrophilic water-insoluble cross-linked polymer swollen with an aqueous impregnant liquid in which the polymer before swelling is capable of absorbing 0.9% by weight saline to form a gel containing at least 50% by weight saline and in which the polymer is formed from 50 to 100% hydroxy alkyl (meth) acrylate in which the alkyl group contains 2 to 4 carbon atoms, and 50 to 0% co-monomer.

2. A package according to claim 1 in which the polymer has been cross-linked by the incorporation of a di- or poly-functional ethylenically unsaturated monomer in the polymerisation mixture.

3. A package according to claim 1 in which the impregnant liquid comprises physiological saline, optionally containing buffer.

4. A package according to claim 1 in which the impregnant liquid contains at least one dissolved therapeutically active substance.

5. A package according to claim 4 in which the therapeutically active substance is a hormone which accelerates wound healing.

6. A package according to claim 1 in which the package is formed from plastics or metal foil.

7. A process for producing a package containing a wound dressing in which a wholly synthetic hydrophilic water-insoluble polymer capable of absorbing 0.9% saline to form a gel comprising at least 50% saline by weight and which has been swollen with an aqueous impregnant liquid is introduced into a flexible package, the package is sealed so as to be moisture-proof and the sealed package is sterilized by heating, whilst exerting external pressure on the package.

8. A process according to claim 7 in which the external pressure is gas pressure and in which sterilisation is carried out by heating in an autoclave.

9. A process according to claim 7, in which the polymer is formed by polymerising monomers, optionally including a water-displaceable diluent and/or water, and in which the polymer produced is subsequently washed to remove water-soluble components, before carrying out the packaging and sterilisation.

10. A process according to claim 7 in which a therapeutically active substance is introduced into the impregnant liquid.

11. A process according to claim 10 in which the therapeutically active substance is incorporated into the impregnant liquid after sterilisation.

12. A process according to claim 11 in which the therapeutically active substance is incorporated into the impregnant liquid before application of the dressing to the wound.

13. A process according to claim 11 in which the therapeutically active substance is incorporated into the impregnant liquid after application of the dressing to the wound.

14. A process according to claim 9 in which the water soluble components are removed by soaking the polymer in several steps in water of different conductivity.

* * * * *